United States Patent
Pichler-Wilhelm et al.

(10) Patent No.: US 11,724,956 B2
(45) Date of Patent: Aug. 15, 2023

(54) GLASS COMPOSITION AND GLASS POWDER, IN PARTICULAR FOR THE USE IN THE DENTAL FIELD

(71) Applicant: SCHOTT AG, Mainz (DE)

(72) Inventors: Sabine Pichler-Wilhelm, Landshut (DE); Jens Suffner, Landshut (DE); Simone Monika Ritter, Mainz (DE)

(73) Assignee: SCHOT T AG, Mainz (DE)

( * ) Notice: Subject to any disclaimer, the term of this patent is extended or adjusted under 35 U.S.C. 154(b) by 320 days.

(21) Appl. No.: 16/941,238

(22) Filed: Jul. 28, 2020

(65) Prior Publication Data
US 2021/0032154 A1    Feb. 4, 2021

(30) Foreign Application Priority Data

Jul. 29, 2019  (DE) .................... 10 2019 120 434.8

(51) Int. Cl.
| | |
|---|---|
| *C03C 3/062* | (2006.01) |
| *A61L 24/12* | (2006.01) |
| *A61K 6/836* | (2020.01) |
| *A61K 6/824* | (2020.01) |

(52) U.S. Cl.
CPC .............. *C03C 3/062* (2013.01); *A61K 6/824* (2020.01); *A61K 6/836* (2020.01); *A61L 24/12* (2013.01); *C03C 2201/12* (2013.01)

(58) Field of Classification Search
CPC ..... C03C 3/062; C03C 2201/12; A61K 6/824; A61K 6/836; A61L 24/12
See application file for complete search history.

(56) References Cited

U.S. PATENT DOCUMENTS

| | | | |
|---|---|---|---|
| 4,927,866 A | 5/1990 | Purrmann et al. |
| 5,215,459 A | 6/1993 | Ney et al. |
| 6,297,181 B1 | 10/2001 | Kunert et al. |
| 7,816,292 B2 | 10/2010 | Zimmer et al. |

FOREIGN PATENT DOCUMENTS

| | | | |
|---|---|---|---|
| CN | 102976618 | | 3/2013 |
| CN | 102976618 A | * | 3/2013 |
| DE | 3806448 | | 9/1989 |
| DE | 4023744 | | 2/1992 |
| DE | 19812278 | | 9/1999 |
| WO | 2005/115936 | | 12/2005 |

OTHER PUBLICATIONS

CN102976618A machine translation (Year: 2013).*
Wilson, Alan D. et al., "Glass-Ionomer Cement", Quintessence books, Quintessence Publishing Co., Inc. 1988, 278 pages.

* cited by examiner

*Primary Examiner* — Karl E Group
*Assistant Examiner* — Cameron K Miller
(74) *Attorney, Agent, or Firm* — Ruggiero McAllister & McMahon LLC

(57) ABSTRACT

The present disclosure relates to a glass composition as well as a glass powder. The disclosure also relates to the use in the dental field, e.g. as dental material such as dental filling or dental restauration material, in particular as or for the production of a glass ionomer cement, for example for the treatment and/or for the filling of cavities in human and/or animal teeth and/or for tooth restoration.

20 Claims, No Drawings

GLASS COMPOSITION AND GLASS POWDER, IN PARTICULAR FOR THE USE IN THE DENTAL FIELD

CROSS-REFERENCE TO RELATED APPLICATION

The present application claims the benefit of German Patent Application No. 10 2019 120 434.8, filed on Jul. 29, 2020, which is herein incorporated by reference.

BACKGROUND OF THE DISCLOSURE

1. Field of the Disclosure

The present disclosure relates to a glass composition as well as a glass powder. The disclosure also relates to the use in the dental field, e.g. as dental material such as dental filling is or dental restauration material, in particular as or for the production of a glass ionomer cement, for example for the treatment and/or for the filling of cavities in human and/or animal teeth and/or for tooth restoration.

2. Background of the Disclosure

Glass ionomer cements are a special product class of dental materials. They are a hybrid material of organic (polyelectrolyte) and inorganic components which sets under the formation of a gel which is the product of an acid/base reaction. Normally, the inorganic component is a fluoroaluminosilicate glass and it actively influences the reaction, the setting behavior as well as the material properties of the subsequent cements. They have been known since the 1960s. Glass ionomer cements are described in detail in "Glasionomerzement" of Alan D. Wilson/John W. McLean, published by the Quintessenz Verlag 1988 ("Wilson").

As a required ratio of $Al_2O_3/SiO_2$ for the formation of cement a value of at least 0.5 is described, wherein with increasing value the compressive strength of the hardened cement rises and the setting time declines. When the value is about 0.75, the setting time runs through a minimum, but in the case of contents of >0.75 it rises only very moderately, while the strength further increases. This e.g. applies to G200 which is also described in "Wilson" (p. 22). Further commercially available glasses are known. Some known glasses have good setting properties and a good strength, but the high initial reactivity reduces the processing time during a dental treatment (filling or restoration) and/or at the dentist such that the glass can only be processed via a subsequent treatment (e.g. acid washing) after the milling. In addition, in most cases they are transparent for X-rays, i.e. on the X-ray film they cannot be distinguished from the dental hard tissue. Generally, low refractive indices of the known glasses are advantageous, because thereby they fit well to the also used acids (e.g. polyacrylic acid with $nd\sim1.43$).

DE 198 12 278 A1 discloses the use of an apatite glass ceramic as biomaterial in the dental field. Thus, a glass ceramic, and not a glass is described. This is a composition with a considerable tendency to crystallization. On the one hand, crystallization results in a plurality of grain boundaries, and on the other hand, the anisotropic behavior of the crystallites results in different refractive indices in various space dimensions, so that an increased scattering and thus opacity of the cement results. However, in the case of a glass ionomer cement the resulting reduction of the aesthetics is not desired. In addition, the disclosed composition contains less complexing agent(s), and thus in total it is chemically so stable that within an acceptable time no dissolution and setting occurs. Furthermore, the material is characterized by X-ray invisibility.

U.S. Pat. No. 6,297,181 B1 discloses a dental glass for the use as glass powder for the production of composites. A use of the glass for the production of glass ionomers is not disclosed. The dental glass has a broad composition range with a high proportion of the constituents $B_2O_3$, ZnO, $ZrO_2$ and $La_2O_3$. However, barium as X-ray absorbing component is not provided in it. In addition, the fluorine containing compositions have very high contents of $B_2O_3$. Also, the refractive indices are very high.

WO 2005/115936 A2 discloses a glass or glass ceramic powder which can be used in the dental field. In the examples carried out, however, only inert dental glass compositions are disclosed which are not suitable for a use as starting glass of a glass ionomer cement.

SUMMARY OF THE DISCLOSURE

Thus, it is an object of the present disclosure to overcome the disadvantages of current glasses. It is an object of the present disclosure to improve the X-ray visibility of the glass. One object of the disclosure is also the reduction of the initial reactivity. Here, the glass should have a low refractive index and good mechanical properties.

The object is solved by the subject matter of the patent claims. The object is in particularly solved by a glass comprising the following components in % by weight:

| Component | Proportion (% by weight) |
| --- | --- |
| component 1 | 22 to 42 |
| component 2 | 28 to 53 |
| component 3 | 5 to 35 |
| component 4 | >5 to 20 | wherein component 1 is selected from the group consisting of $SiO_2$, $P_2O_5$ and combinations of both, wherein component 2 is selected from the group consisting of MgO, CaO, SrO, BaO, ZnO, $Al_2O_3$, $Sc_2O_3$, $Y_2O_3$, $La_2O_3$, $Yb_2O_3$ as well as combinations of two or more thereof, wherein component 3 is selected from the group consisting of $Li_2O$, $Na_2O$, $K_2O$, $Cs_2O$ and combinations of two or more thereof, wherein component 4 is F, wherein the glass contains at least one X-ray absorbing component of the group consisting of $Y_2O_3$, $Yb_2O_3$, $La_2O_3$, SrO, BaO and $Cs_2O$, wherein the total content of $B_2O_3$, ZnO, $ZrO_2$ and $La_2O_3$ is less than 20% by weight and wherein the glass contains less than 5% by weight of $B_2O_3$.

In particular, the glass of the present disclosure is not a glass ceramic. Thus, advantageously, it is not present in crystallized form. Apart from that, of course, it is possible and the disclosure comprises that in volume and/or surface areas crystal phases may be present which may be generated, for example, by surface crystallization.

DETAILED DESCRIPTION OF THE DISCLOSURE

The glass of the present disclosure contains the above described components 1 to 4 which according to their prevailing function may in particularly also be referred to as glass formers (component 1), matrix formers (component 2), reaction accelerators (component 3) and complexing agents (component 4). Besides the constituents mentioned, the glass may contain further constituents which may also have a function as glass former, matrix former, reaction accelerator or complexing agent, and/or another function. However, particularly preferably, besides the constituents of the components 1, 2, 3 and 4 mentioned, the glass contains only low amounts of further constituents having a function as glass former, matrix former, reaction accelerator or complexing agent or no further constituents with one of the functions mentioned at all.

The proportion of further glass formers which in addition are present in the glass is preferably at most 10% by weight, further preferably at most 5% by weight, further preferably at most 2% by weight, further preferably at most 1% by weight, further preferably at most 0.5% by weight, further preferably at most 0.2% by weight, further preferably at most 0.1% by weight. Particularly preferably, the glass does not contain further glass formers.

The proportion of matrix formers which in addition are present in the glass is preferably at most 10% by weight, further preferably at most 5% by weight, further preferably at most 2% by weight, further preferably at most 1% by weight, further preferably at most 0.5% by weight, further preferably at most 0.2% by weight, further preferably at most 0.1% by weight. Particularly preferably, the glass does not contain further matrix formers.

The proportion of reaction accelerators which in addition are present in the glass is preferably at most 10% by weight, further preferably at most 5% by weight, further preferably at most 2% by weight, further preferably at most 1% by weight, further preferably at most 0.5% by weight, further preferably at most 0.2% by weight, further preferably at most 0.1% by weight. Particularly preferably, the glass does not contain further reaction accelerators.

The proportion of complexing agents which in addition are present in the glass is preferably at most 10% by weight, further preferably at most 5% by weight, further preferably at most 2% by weight, further preferably at most 1% by weight, further preferably at most 0.5% by weight, further preferably at most 0.2% by weight, further preferably at most 0.1% by weight. Particularly preferably, the glass does not contain further complexing agents.

When the proportion of component 1 is too high, then this results, besides relatively high melting temperatures, in increased acid resistances so that the glass cannot react within a sufficiently short period of time. Due to the increased acid resistance the proportion of component 2, which is released by acid, becomes low so that the cement forming properties are impaired and the production of a glass ionomer cement mediated by acid addition is considerably impeded. On the other hand, a starting glass with a content of component 1 which is too low results in poorly meltable compositions with undesirably high refractive indices.

A proportion of component 3 (alkalis) which is too low results in relatively resistant glasses with low reactivity. A proportion which is too high is particularly disadvantageous for the initial cement forming reaction, because thereby only little time for homogenizing and processing the filling is available. Proportions of component 3 which are too high result in glasses which tolerate processing times of the cement which are too short.

The role of the component 4 is to bind the released metal ions of the group of the network formers in a complex for a short time. This delays the bonding of the cations at the negatively charged sites of the polyelectrolyte chain so that the gel formation is postponed and thus the processing time is extended. In addition, the complex formation also results in a release of protons so that the acidity of the paste is increased and thus the gel formation which depends on the pH value is postponed. Systems without complexing agent(s) are not capable of forming resistant cements so that a complexing agent has to be present in the glass. A proportion of complexing agent which is too low is disadvantageous, because in such a case the speed of the setting is accelerated. On the other hand, a proportion which is too high results in glasses with a strong tendency to segregation and which during melting are subject to strong evaporation of the complexing agents. In particular, segregation leads in the case of fillings to unaesthetic results.

The component 1 is selected from the group consisting of $SiO_2$, $P_2O_5$ and combinations of both. Preferably, the component 1 comprises $SiO_2$ and $P_2O_5$. For the formation of cement the component 1 may also function as host lattice for the soluble ions. Preferably, the proportion of the component 1 is in a range of 22 to 42% by weight, further preferably of 24 to 40% by weight, still further preferably of 25 to 37% by weight, still further preferably of 26 to 35% by weight.

The component 2 is selected from the group consisting of MgO, CaO, SrO, BaO, ZnO, $Al_2O_3$, $Sc_2O_3$, $Y_2O_3$, $La_2O_3$, $Yb_2O_3$ and combinations of two or more thereof. Preferably, the component 2 is selected from the group consisting of $Al_2O_3$, CaO, SrO, BaO and combinations of two or more thereof. Particularly preferably, the component 2 comprises $Al_2O_3$. Preferably, the proportion of the component 2 is in a range of 28 to 53% by weight, further preferably of 29 to 53% by weight, further preferably of 30 to 51% by weight, still further preferably of 31 to 48% by weight.

The component 3 is selected from the group consisting of $Li_2O$, $Na_2O$, $K_2O$, $Cs_2O$ and combinations of two or more thereof. Particularly preferably, the component 3 comprises $Na_2O$ and/or $Cs_2O$. Especially preferably, the component 3 comprises $Cs_2O$. Still further preferably, the component 3 is $Cs_2O$. Preferably, the proportion of the component 3 is in a range of 5 to 35% by weight, further preferably of 6 to 32% by weight, further preferably of 8 to 30% by weight, still further preferably of 9 to 29% by weight.

The component 4 is F. Preferably, the proportion of the component 4 is in a range of >5 to 20% by weight, further preferably of 6 to 20% by weight, further preferably of 7 to 20% by weight, further preferably of 8 to 20% by weight, further preferably of 9 to 19% by weight, further preferably of 9.5 to 18% by weight, still further preferably of 9.5 to 17.5% by weight. A minimum content of component 4 of at least 9.5% by weight, further preferably at least 10% by weight is particularly preferable.

By the use of F and due to its release the teeth can be remineralized through the formation of fluorapatite. Fluorapatite in the dental hard tissue is a compound which originates from hydroxyl apatite after the substitution of the hydroxide ions by fluoride ions.

When relatively light-weight elements or their oxides of the respective groups of the components 1 to 4 are used, low refractive indices nd of <1.50 can be achieved. Thereby, the difference of the refractive index with respect to polyacrylic acid is lower than in the case of the use of more heavy-weight elements. Thus, in particular, the glasses can be used well as or for aesthetically improved glass ionomer cements.

However, when the glasses should be used as a component in resin-reinforced glass ionomer cements, a slightly higher refractive index of about nd=1.52 is more favorable for achieving particularly advantageous aesthetic results. This, for example, can be achieved by the use of more heavy-weight elements.

The glass of the disclosure contains at least one X-ray absorbing component selected from the group consisting of $Y_2O_3$, $Yb_2O_3$, $La_2O_3$, SrO, BaO and $Cs_2O$, preferably in a proportion of in total at least 0.1% by weight. Preferably, the glass contains at least one X-ray absorbing component from the group consisting of SrO, BaO and $Cs_2O$. Preferably, the proportion of the X-ray absorbing components is in total even at least 0.5% by weight, further preferably at least 2% by weight, further preferably at least 5% by weight, further preferably at least 15% by weight, further preferably at least 20% by weight. But the proportion of the X-ray absorbing components should also not be too high, and is in total preferably at most 55% by weight, further preferably at most 45% by weight, further preferably at most 43% by weight. Preferably, the total proportion of the X-ray absorbing components is in a range of 1 to 50% by weight, further preferably of 5 to 45% by weight, further preferably of 15 to 43% by weight.

Preferably, the glass of the disclosure comprises the following components in % by weight:

| Component | Proportion (% by weight) |
|---|---|
| component 1 | 24 to 40 |
| component 2 | 29 to 53 |
| component 3 | 6 to 32 |
| component 4 | 9 to 19 |

Further preferably, the glass comprises the following components in % by weight:

| Component | Proportion (% by weight) |
|---|---|
| component 1 | 25 to 37 |
| component 2 | 30 to 51 |
| component 3 | 8 to 30 |
| component 4 | 9.5 to 18 |

Still further preferably, the glass comprises the following components in % by weight:

| Component | Proportion (% by weight) |
|---|---|
| component 1 | 26 to 35 |
| component 2 | 31 to 48 |
| component 3 | 9 to 29 |
| component 4 | 9.5 to 17.5 |

Preferably, the glass comprises the following constituents in % by weight:

| Constituent | Proportion (% by weight) |
|---|---|
| $SiO_2$ | 15 to 35 |
| $P_2O_5$ | 3 to 12 |
| $Al_2O_3$ | 15 to 35 |
| CaO | 0 to 13 |
| SrO | 0 to 22 |
| BaO | 0 to 28 |
| $Na_2O$ | 0 to 12 |
| $Cs_2O$ | 0 to 35 |
| F | >5 to 20 |

Preferably, the glass contains $SiO_2$ in a proportion of 15 to 35% by weight, further preferably of 15 to 34% by weight, further preferably of 16 to 32% by weight, further preferably of 17 to 30% by weight.

Preferably, the glass contains $P_2O_5$ in a proportion of 3 to 12% by weight, further preferably of 3 to 11.5% by weight, further preferably of 4 to 11% by weight, further preferably of 4.5 to 10% by weight, further preferably of 5 to 9% by weight. Particularly preferably, the proportion of $P_2O_5$ is even only at most 8.5% by weight.

Preferably, the glass contains $Al_2O_3$ in a proportion of 15 to 35% by weight, further preferably of 16 to 35% by weight, further preferably of 17 to 32% by weight, further preferably of 18 to 31% by weight, further preferably of 19 to 30% by weight.

Preferably, the glass contains CaO in a proportion of 0 to 13% by weight, further preferably of 0.5 to 12% by weight, further preferably of 1 to 11% by weight, further preferably of 1.5 to 10.5% by weight, further preferably of 2 to 10% by weight. In some embodiments of the disclosure the content of CaO is preferably less than 0.5% by weight, further preferably less than 0.4% by weight, further preferably less than 0.3% by weight, further preferably less than 0.2% by weight, further preferably less than 0.1% by weight, or the glass is even free of CaO.

Preferably, the glass contains SrO in a proportion of 0 to 22% by weight, further preferably 0.1 to 21% by weight, further preferably 0.5 to 20.5% by weight, further preferably 1 to 20% by eight, further preferably 2 to 19% by weight, further preferably 3 to 16% by weight. In some embodiments, the proportion of SrO is preferably even at most 15% by weight, further preferably at most 9% by weight, further preferably at most 8% by weight, further preferably at most 7% by weight, further preferably at most 5% by weight. In some embodiments, the content of SrO is preferably less than 0.5% by weight, further preferably less than 0.4% by weight, further preferably less than 0.3% by weight, further preferably less than 0.2% by weight, further preferably less than 0.1% by weight, or the glass of the disclosure is even free of SrO.

Preferably, the glass contains BaO in a proportion of 0 to 28% by weight, further preferably of 0.1 to 27% by weight, further preferably 0.5 to 26.5% by weight, further preferably of 1 to 26% by weight, further preferably 2 to 26% by weight, further preferably of 5 to 25.5% by weight, further preferably of 6 to 21% by weight. In some embodiments, the proportion of BaO is preferably even at most 20% by weight, further preferably at most 13% by weight, further preferably at most 9% by weight. In some embodiments of the disclosure the content of BaO is preferably less than 0.5% by weight, further preferably less than 0.4% by weight, further preferably less than 0.3% by weight, further preferably less than 0.2% by weight, further preferably less than 0.1% by weight, or the glass is even free of BaO.

Preferably, the glass contains $Na_2O$ in a proportion of 0 to 12% by weight, further preferably of 0 to 11% by weight, further preferably of 0 to 10.5% by weight, further preferably of 1 to 10% by weight. In some embodiments, the proportion of $Na_2O$ is preferably even at most 9.5% by weight, further preferably at most 8% by weight, further preferably at most 4% by weight. In some embodiments of the disclosure the content of $Na_2O$ is preferably less than 0.5% by weight, further preferably less than 0.4% by weight, further preferably less than 0.3% by weight, further preferably less than 0.2% by weight, further preferably less than 0.1% by weight, or the glass is even free of $Na_2O$.

Preferably, the glass contains $Cs_2O$ in a proportion of 0 to 35% by weight, further preferably of 0.1 to 34.5% by weight, further preferably 0.5 to 34% by weight, further preferably 1 to 33.5% by weight, further preferably 2 to 33% by weight, further preferably of 5 to 32% by weight, further preferably of 10 to 31% by weight, further preferably of 12 to 30% by weight. In some embodiments, the proportion of $Cs_2O$ is preferably even at most 28% by weight, further preferably at most 18% by weight, further preferably at most 17% by weight. In some embodiments of the disclosure the content of $Cs_2O$ is preferably less than 0.5% by weight, further preferably less than 0.4% by weigh, further preferably less than 0.3% by weight, further preferably less than 0.2% by weight, further preferably less than 0.1% by weight, or the glass is even free of $Cs_2O$.

Preferably, the glass contains F in a proportion of >5 to 20% by weight, further preferably of 6 to 20% by weight, further preferably of 7 to 20% by weight, further preferably of 8 to 20% by weight, further preferably of 9 to 19% by weight, further preferably of 9.5 to 18% by weight, 9.5 to 17.5% by weight, further preferably of 10 to 11% by weight. In some embodiments, the proportion of F is preferably at least 9.5% by weight, further preferably at least 10% by weight or even higher than 10% by weight.

$B_2O_3$ for supporting the adjustment of the melting behavior can be omitted since the glasses of the present disclosure already contain relatively high amounts of F. Glasses which contain $B_2O_3$ in significant amounts have even shown to be disadvantageous for this purpose, because $B_2O_3$ just as F further reduces the melting temperature, which may lead to the fact that other constituents of the glass only melt insufficiently or not at all, or that it can lead to excessive evaporation, in particular of the fluorine components i.e., when the temperature is increased again for the melting of these constituents. Therefore, the glasses of the present disclosure contain less than 5% by weight, preferably less than 4% by weight, further preferably less than 3% by weight, further preferably less than 2% by weight, further preferably less than 1% by weight, further preferably less than 0.75% by weight, further preferably less than 0.5% by weight, further preferably less than 0.4% by weight, further preferably less than 0.3% by weight, further preferably less than 0.2% by weight, further preferably less than 0.1% by weight of $B_2O_3$. Particularly preferably, the glasses are free of $B_2O_3$.

Furthermore, it has been shown that also ZnO, $ZrO_2$ and $La_2O_3$ should not be used in too high amounts, so that in particular the refractive index is not increased too strong. A limitation of the content of the mentioned constituents in particularly also pertains in connection with $B_2O_3$. The total content of $B_2O_3$, ZnO, $ZrO_2$ and $La_2O_3$ in the glasses is less than 20% by weight, preferably less than 15% by weight, preferably less than 10% by weight, preferably less than 5% by weight, preferably less than 2% by weight, preferably less than 1% by weight, further preferably less than 0.75% by weight, further preferably less than 0.5% by weight, further preferably less than 0.4% by weight, further preferably less than 0.3% by weight, further preferably less than 0.2% by weight, further preferably less than 0.1% by weight. Particularly preferably, the glasses are free of $B_2O_3$, ZnO, $ZrO_2$ and $La_2O_3$.

The glasses of the present disclosure preferably contain less than 0.5% by weight, further preferably less than 0.4% by weight, further preferably less than 0.3% by weight, further preferably less than 0.2% by weight, further preferably less than 0.1% by weight of $Tb_2O_3$ and/or $Eu_2O_3$. Particularly preferably, the glasses are free of $Tb_2O_3$ and $Eu_2O_3$. Thus, preferably, the glasses contain neither $Tb_2O_3$ nor $Eu_2O_3$.

The glasses of the present disclosure may contain $Y_2O_3$. However, preferably, the content of $Y_2O_3$ is less than 1% by weight, further preferably less than 0.75% by weight, further preferably less than 0.5% by weight, further preferably less than 0.4% by weight, further preferably less than 0.3% by weight, further preferably less than 0.2% by weight, further preferably less than 0.1% by weight. Particularly preferably, the glasses are free of $Y_2O_3$.

The glasses of the present disclosure may contain $Sc_2O_3$. However, preferably, the content of $Sc_2O_3$ is less than 1% by weight, further preferably less than 0.75% by weight, further preferably less than 0.5% by weight, further preferably less than 0.4% by weight, further preferably less than 0.3% by weight, further preferably less than 0.2% by weight, further preferably less than 0.1% by weight. Particularly preferably, the glasses are free of $Sc_2O_3$.

The glasses of the present disclosure may contain $La_2O_3$. However, preferably, the content of $La_2O_3$ is less than 1% by weight, further preferably less than 0.75% by weight, further preferably less than 0.5% by weight, further preferably less than 0.4% by weight, further preferably less than 0.3% by weight, further preferably less than 0.2% by weight, further preferably less than 0.1% by weight. Particularly preferably, the glasses are free of $La_2O_3$.

The glasses of the present disclosure may contain $Yb_2O_3$. However, preferably, the content of $Yb_2O_3$ is less than 1% by weight, further preferably less than 0.75% by weight, further preferably less than 0.5% by weight, further preferably less than 0.4% by weight, further preferably less than 0.3% by weight, further preferably less than 0.2% by weight, further preferably less than 0.1% by weight. Particularly preferably, the glasses are free of $Yb_2O_3$.

When in this description it is mentioned that the glasses are free of a constituent or that the glasses do not contain a certain constituent, then this means that it is only allowed for this constituent to be present as an impurity in the glasses. This means that said constituent is not added in substantial amounts. According to the present disclosure, not substantial amounts are amounts of less than 500 ppm, preferably less than 300 ppm, particularly preferably less than 100 ppm and most preferably less than 50 ppm, based on the proportion by weight.

Preferably, the ratio of the sum of the proportions by weight of $Al_2O_3$, $Sc_2O_3$, $Y_2O_3$, $La_2O_3$ and $Yb_2O_3$ to the proportion by weight of $SiO_2$ is higher than 0.75:1, further preferably higher than 0.8:1, further preferably higher than 0.9:1, further preferably higher than 0.95:1, further preferably higher than 0.96:1, further preferably higher than 0.97:1, further preferably higher than 0.98:1, further preferably higher than 0.99:1, further preferably higher than 1.0:1. Further preferably, the ratio of the sum of the proportions by weight of $Al_2O_3$, $Sc_2O_3$, $Y_2O_3$, $La_2O_3$ and $Yb_2O_3$ to the proportion by weight of $SiO_2$ is in a range of 0.9:1 bis 1.15:1, further preferably of 0.95:1 to 1.1:1. Particularly preferably, the ratio of the proportion by weight of $Al_2O_3$ to the proportion by weight of $SiO_2$ is higher than 0.75:1, further preferably higher than 0.8:1, further preferably higher than 0.9:1, further preferably higher than 0.95:1, further preferably higher than 0.96:1, further preferably higher than 0.97:1, further preferably higher than 0.98:1, further preferably higher than 0.99:1, further preferably higher than 1.0:1. Especially preferably, the ratio of the proportion by weight of $Al_2O_3$ to the proportion by weight of $SiO_2$ is in a range of 0.9:1 to 1.15:1, further preferably of 0.95:1 to 1.1:1.

Preferably, the ratio of the proportion by weight of the component 2 to the proportion by weight of the component 1 is in a range of 1.0:1 to 1.6:1, further preferably of 1.1:1 to 1.5:1, further preferably of 1.2:1 to 1.4:1, further preferably of 1.25:1 to 1.35:1. It is particularly advantageous, when the ratio of the proportion by weight of the component 2 to the proportion by weight of the component 1 is at least 1.15:1, further preferably at least 1.2:1, further preferably at least 1.25:1. If the ratio of the proportion by weight of the component 2 to the proportion by weight of the component 1 is low, the compressive strength of the set cement may be low. Furthermore, a low ratio may be associated with high melting temperatures (and in turn increased evaporation of F) and high acid resistance so that the reactivity may be reduced. On the other hand, if the ratio of the proportion by weight of the component 2 to the proportion by weight of the component 1 is high, the refractive index may be high, the reaction time may be low and the setting time may be high. Furthermore, there may be an undesirably high and unaesthetic visual opacity.

Preferably, the ratio of the proportion by weight of the component 2 to the proportion by weight of the component 3 is in a range of 1.0:1 to 6.5:1, further preferably of 1.1:1 to 5.5:1, further preferably of 1.2:1 to 4.5:1. This is advantageous for reducing the risk of devitrification. Particularly preferably, the ratio of the proportion by weight of the component 2 to the proportion by weight of the component 3 is at most 4.0:1, further preferably at most 3.0:1, further preferably at most 2.5:1, further preferably at most 2.0:1, further preferably at most 1.75:1, further preferably at most 1.5:1, further preferably at most 1.4:1. If the ratio of the proportion by weight of the component 2 to the proportion by weight of the component 3 is high, there is an increased risk of devitrification/crystallization. Furthermore, the reactivity (dissolution of the glass) may be low. On the other hand, if the ratio of the proportion by weight of the component 2 to the proportion by weight of the component 3 is low, the reactivity may be very high so that the processing time is low. Furthermore, chemical resistance and hardness of the cement may be reduced.

Preferably, the ratio of the proportion by weight of the component 2 to the proportion by weight of the component 4 is in a range of 3.0:1 to 4.5:1, further preferably of 3.1:1 to 4.0:1, further preferably of 3.2:1 to 3.6:1, further preferably of 3.25:1 to 3.55:1. This is advantageous with respect to refractive index and X-ray opacity. It is particularly advantageous, when the ratio of the proportion by weight of the component 2 to the proportion by weight of the component 4 is at least 3.1:1, further preferably at least 3.2:1, further preferably at least 3.25:1. If the ratio of the proportion by weight of the component 2 to the proportion by weight of the component 4 is low, there may be segregation resulting in aesthetically unsatisfactory restauration. Furthermore, the production of the glass may be complicated. On the other hand, if the ratio of the proportion by weight of the component 2 to the proportion by weight of the component 4 is high, resistance and lifetime of the cement may be reduced.

Preferably, the ratio of the proportion by weight of the component 1 to the proportion by weight of the component 3 is in a range of 0.8:1 to 4.5:1, further preferably of 0.9:1 to 4.1:1. It is particularly advantageous, when the ratio of the proportion by weight of the component 1 to the proportion by weight of the component 3 is at most 4.0:1, further preferably at most 3.5:1, further preferably at most 3.0:1, further preferably at most 2.5:1, further preferably at most 2.0:1, further preferably at most 1.8:1, further preferably at most 1.75:1, further preferably at most 1.5:1, further preferably at most 1.25:1, further preferably at most 1.2:1, further preferably at most 1.15:1, further preferably at most 1.1:1. If the ratio of the proportion by weight of the component 1 to the proportion by weight of the component 3 is high, melting temperatures may be high so that there may be increased evaporation of F. Furthermore, the reaction speed may be low so that there are long processing times or processing may be deteriorated. On the other hand, if the ratio of the proportion by weight of the component 1 to the proportion by weight of the component 3 is low, chemical resistance may be low and reactivity may be high so that there are reduced processing times of the cement.

Preferably, the ratio of the proportion by weight of the component 1 to the proportion by weight of the component 4 is in a range of 2.0:1 to 4.0:1, further preferably of 2.25:1 to 3.5:1, further preferably of 2.4:1 to 3.0:1, further preferably of 2.45:1 to 2.85:1, further preferably of 2.5:1 to 2.8:1. If the ratio of the proportion by weight of the component 1 to the proportion by weight of the component 4 is low, the gel formation may be very fast and the processing time may be reduced. On the other hand, if the ratio of the proportion by weight of the component 1 to the proportion by weight of the component 4 is high, the durability of the cements may be reduced and the setting speed may be increased.

Preferably, the ratio of the proportion by weight of the component 3 to the proportion by weight of the component 4 is in a range of 0.6:1 to 4.0:1, further preferably of 0.7:1 to 3.5:1, further preferably of 0.8:1 to 3.0:1, further preferably of 1.0:1 to 2.9:1, further preferably of 1.5:1 to 2.8:1, further preferably of 2.0:1 to 2.7:1, further preferably of 2.25:1 to 2.65:1, further preferably of 2.5:1 to 2.6:1. It is particularly advantageous, when the ratio of the proportion by weight of the component 3 to the proportion by weight of the component 4 is at least 0.8:1, further preferably at least 1.0:1, further preferably at least 1.5:1, further preferably at least 1.7:1, further preferably at least 2.0:1, further preferably at least 2.1:1, further preferably at least 2.2:1, further preferably at least 2.3:1, further preferably at least 2.4:1, further preferably at least 2.5:1. If the ratio of the proportion by weight of the component 3 to the proportion by weight of the component 4 is low, there may be increased evaporation of F. Production of the glass may be complicated. Furthermore, resistance and lifetime of the cement may be reduced. On the other hand, if the ratio of the proportion by weight of the component 3 to the proportion by weight of the component 4 is high, the refractive index may be high. Furthermore, the reactivity may be high, processing time and chemical resistance may be low and hardness of the cement may be reduced.

The glasses of the present disclosure have preferably a refractive index nd of at most 1.55. Preferably, the refractive index nd of the glasses of the present disclosure is in a range of 1.43 to 1.55, further preferably of 1.44 to 1.52, further preferably in a range of 1.45 to <1.50. The low refractive indices are advantageous, because they fit well to the also used acids (e.g. polyacrylic acid with nd of about 1.43), so that a good optical impression of the materials results.

The density of the glasses of the disclosure is preferably less than 3.3 $g/cm^3$, further preferably less than 3.15 $g/cm^3$, further preferably less than 3.0 $g/cm^3$, further preferably less than 2.9 $g/cm^3$, further preferably less than 2.8 $g/cm^3$.

According to DIN ISO 4049, the X-ray opacity of dental glasses or materials is indicated in relation to the X-ray absorption of aluminum as aluminum equivalent thickness (ALET). Thus, an ALET of 200% means that a glass plate having plane-parallel surfaces with a thickness of 2 mm produces the same X-ray attenuation as an aluminum plate with a thickness of 4 mm. Analogously, an ALET of 500% means that a glass plate having plane-parallel surfaces with a thickness of 2 mm produces the same X-ray attenuation as an aluminum plate with a thickness of 10 mm. In an alternative, the ALET can also be indicated in mm. In this case, the value is the thickness of an aluminum plate which produces the same X-ray attenuation as a glass plate having plane-parallel surfaces with a thickness of 2 mm. Thus, in the above-mentioned example the ALET can be indicated as 500% or as 10 mm. Both values are equivalent.

The ALET of the glasses of the present disclosure is preferably in a range of 100% to 1500%, further preferably of 125% to 1400%, further preferably of 150% to 1300%. Particularly preferably, the ALET of the glasses is in a range of 175% to 1200%, further preferably of 200% to 1100%, still further preferably of 300% to 1100%, still further preferably 400% to 1000%, still further preferably 500% to 1000%. Such glasses have a particularly advantageous X-ray visibility.

The ALET of the glasses of the present disclosure is preferably in a range of 2 mm to 30 mm, further preferably of 2.5 mm to 28 mm, further preferably of 3 mm to 26 mm. Particularly preferably, the ALET of the glasses is in a range of 3.5 mm to 24 mm, further preferably of 4 mm to 22 mm, still further preferably of 6 mm to 20 mm. Such glasses have a particularly advantageous X-ray visibility.

The present disclosure also relates to a glass powder comprising the glass of the disclosure. Preferably, the glass powder consists of the glass of the disclosure.

The particle size of the glass powder, when specified as d50 value, is preferably in a range of 0.2 μm to 20 μm, further preferably 0.3 μm to 15 μm, further preferably of 0.4 μm to 10 μm, further preferably of 0.7 μm to 9 μm, particularly preferably of 1 μm to 8 μm. The d50 value means that 50% of the particles are smaller than the given value. The measurement of the particle sizes is preferably conducted by particle analysis by means of laser diffraction, particularly preferably such as described in the ISO13320:2009. Reaction time and setting time are dependent on the available surface and hence on the particle size distribution. The smaller the particle size of the glass powder is, the faster are the reactions.

The present disclosure also relates to a method for the production of a glass powder according to the present disclosure comprising the following step:

grinding of the glass of the present disclosure.

The selection of desired particle sizes is preferably effected by classifying of the obtained glass powders on a case-by-case basis.

The present disclosure also relates to a method for the production of a glass ionomer cement comprising the following step:

mixing of a glass powder of the present disclosure with an organic acid.

For example, the material can be processed into a paste, which, for example, can be applied as a filling of a tooth cavity.

Preferably, the organic acid is polyacrylic acid, or a copolymer of acrylic acid with itaconic acid and/or maleic acid. Particularly preferably, the organic acid is polyacrylic acid.

The reaction and setting mechanism of the glass may be specifically modified or adjusted. For example, it may be desired to slow down the reaction for the time period in which the mixing takes place (generally the first few minutes), while maintaining a fast subsequent setting mechanism. This may be achieved by washing the glasses with acid for reducing the amount of the easily dissolvable elements of components 2 and 3 at the surface. Silanization is also possible, in particular if the material is intended to be used in resin modified glass ionomer cement materials. Furthermore, thermal treatment above the glass transition temperature may be used to affect reactivity by crystallization.

The present disclosure also relates to a glass ionomer cement comprising the glass powder of the present disclosure. Preferably, the glass ionomer cement has been or can be obtained according to the method for the production of a glass ionomer cement of the disclosure.

The present disclosure also relates to the use of the glass ionomer cement of the disclosure in the dental field.

The present disclosure also relates to a glass and/or glass powder according to the present disclosure for the production of a glass ionomer cement. The present disclosure also relates to the use of a glass and/or glass powder according to the present disclosure for the production of a glass ionomer cement.

The present disclosure also relates to a filling material for the production of glass ionomer cements for dental uses, in particular for the production of dental prosthetics and/or the filling of cavities, comprising the glass and/or the glass powder of the present disclosure. The disclosure also relates to the use of a glass and/or glass powder according to the present disclosure for the production of glass ionomer cements for dental uses, in particular for the production of dental prosthetics and/or the filling of cavities.

The present disclosure also relates to a glass and/or glass powder according to the present disclosure for providing a therapeutic or prosthetic substance mixture, in particular for use in dentistry, preferably for the filling of cavities in human and/or animal teeth and/or for tooth restoration, for example for use in the treatment of caries. The present disclosure also relates to the use of a glass and/or glass powder according to the present disclosure for providing a therapeutic or prosthetic substance mixture, in particular for use in dentistry, preferably for the filling of cavities in human and/or animal teeth and/or for tooth restoration, for example for use in the treatment of caries.

The present disclosure also relates to the glass and/or glass powder according to the present disclosure and/or the glass ionomer cement according to the present disclosure for use in medicine, in particular in dentistry and/or odontology. The present disclosure also relates to the glass and/or glass powder according to the present disclosure and/or the glass ionomer cement according to the present disclosure for use in the treatment, in particular filling, of cavities in human and/or animal teeth and/or for tooth restoration. The present disclosure also relates to the glass and/or glass powder according to the present disclosure and/or the glass ionomer cement according to the present disclosure for use in treatment of caries.

The present disclosure also relates to the use of the glass of the disclosure for the production of a chemically hardening composite, wherein the composite may have the form of a surface-covering layer, or for the production of an adhesive composite between at least two materials from the field of metals and inorganic nonmetal substances.

In a further aspect, the present disclosure also relates to a glass based substance or substance mixture for the preparation of a glass ionomer cement with prolonged processing time, comprising a reactive component 3 which influences the processing time of the initial cement forming reaction, and a component 4, which delays the bonding of cations at the negatively charged sites of the polyelectrolyte chain of the ionomer cement, whereas the ratio of the proportion by weight of the component 3 to the proportion by weight of the component 4 is at least 2.0:1, further preferably at least 2.1:1, further preferably at least 2.2:1, further preferably at least 2.3:1, further preferably at least 2.4:1, further preferably at least 2.5:1. Preferably, the ratio of the proportion by weight of the component 3 to the proportion by weight of the component 4 is in a range of from 2.0:1 to 4.0:1, for example from 2.1:1 to 3.75:1, from 2.2:1 to 3.5:1, from 2.3:1 to 3.25:1, from 2.4:1 to 3.0:1, or from 2.5:1 to 2.8:1. Preferably, component 3 is selected from the group consisting of $Li_2O$, $Na_2O$, $K_2O$, $Cs_2O$ and combinations of two or more thereof, and the component 4 is F.

The disclosure also relates to a glass and/or glass powder for the preparation of a glass ionomer cement, in particular a glass ionomer cement with prolonged processing time. The glass and/or glass powder comprises a reactive component 3 which preferably influences the processing time of the initial cement forming reaction, and a component 4 which preferably delays the bonding of cations at the negatively charged sites of the polyelectrolyte chain of the ionomer cement, wherein the ratio of the proportion by weight of the component 3 to the proportion by weight of the component 4 is at least 2.0:1, further preferably at least 2.1:1, further preferably at least 2.2:1, further preferably at least 2.3:1, further preferably at least 2.4:1, further preferably at least 2.5:1. Preferably, the ratio of the proportion by weight of the component 3 to the proportion by weight of the component 4 is in a range of from 2.0:1 to 4.0:1, for example from 2.1:1 to 3.75:1, from 2.2:1 to 3.5:1, from 2.3:1 to 3.25:1, from 2.4:1 to 3.0:1, or from 2.5:1 to 2.8:1. Preferably, component 3 is selected from the group consisting of $Li_2O$, $Na_2O$, $K_2O$, $Cs_2O$ and combinations of two or more thereof, and the component 4 is F.

The disclosure also relates to a glass and/or glass powder comprising a component 3 selected from the group consisting of $Li_2O$, $Na_2O$, $K_2O$, $Cs_2O$ and combinations of two or more thereof, and a component 4 being F, wherein the ratio of the proportion by weight of the component 3 to the proportion by weight of the component 4 is at least 2.0:1, further preferably at least 2.1:1, further preferably at least 2.2:1, further preferably at least 2.3:1, further preferably at least 2.4:1, further preferably at least 2.5:1. Preferably, the ratio of the proportion by weight of the component 3 to the proportion by weight of the component 4 is in a range of from 2.0:1 to 4.0:1, for example from 2.1:1 to 3.75:1, from 2.2:1 to 3.5:1, from 2.3:1 to 3.25:1, from 2.4:1 to 3.0:1, or from 2.5:1 to 2.8:1.

EXAMPLES

The following table shows composition and properties of the example glasses 4 to 13 according to the present disclosure as well as of the comparative examples 1 to 3 which are not according to the present disclosure. Each composition is given in % by weight. The comparative examples do not contain an X-ray absorbing component and have a low ALET.

| | Ex 1 | Ex 2 | Ex 3 | Ex 4 | Ex 5 | Ex 6 | Ex 7 | Ex 8 | Ex 9 | Ex 10 | Ex 11 | Ex 12 | Ex 13 |
|---|---|---|---|---|---|---|---|---|---|---|---|---|---|
| $Si_2O$ | 29.7 | 27.2 | 26.9 | 23.5 | 27.6 | 21.8 | 25.1 | 20.3 | 23.5 | 24.3 | 25.3 | 21.0 | 24.3 |
| $P_2O_5$ | 8.3 | 7.6 | 7.6 | 6.6 | 7.8 | 6.1 | 7.1 | 5.7 | 6.6 | 6.8 | 7.1 | 5.8 | 6.8 |
| $Al_2O_3$ | 28.8 | 29.7 | 29.4 | 22.9 | 26.8 | 21.2 | 24.3 | 19.7 | 22.7 | 23.5 | 24.5 | 20.9 | 23.5 |
| CaO | 10.8 | 9.7 | 9.6 | 8.6 | | | | | | 4.5 | 4.6 | 2.6 | 2.9 |
| SrO | | | | | 18.1 | 14.4 | | | 7.8 | | 8.3 | 4.7 | 5.4 |
| BaO | | | | | | | 24.5 | 19.9 | 11.5 | 11.9 | | 7.0 | 8.1 |
| $Na_2O$ | 9.4 | 9.4 | 9.3 | | 8.8 | | 8.0 | | 3.7 | 3.8 | 4.0 | | 3.8 |
| $Cs_2O$ | | | | 28.2 | | 26.1 | | 24.3 | 14.0 | 14.5 | 15.1 | 27.5 | 14.5 |
| F | 13.0 | 16.4 | 17.2 | 10.3 | 10.9 | 10.3 | 11.0 | 10.1 | 10.3 | 10.6 | 11.1 | 10.6 | 10.6 |
| sum | 100 | 100 | 100 | 100 | 100 | 100 | 100 | 100 | 100 | 100 | 100 | 100 | 100 |
| Properties | | | | | | | | | | | | | |
| $n_d$ | 1.468 | 1.468 | 1.468 | 1.483 | 1.474 | 1.492 | 1.496 | 1.497 | 1.484 | 1.483 | 1.477 | 1.490 | 1.480 |
| density [g/cm³] | 2.60 | 2.60 | 2.60 | 2.92 | 2.80 | 3.11 | 3.00 | 3.26 | 3.07 | 2.98 | 2.89 | 3.11 | 2.99 |
| ALET [%] | 89 | 86 | 85 | 109 | 342 | 1108 | 612 | 1218 | 904 | 717 | 618 | 1086 | 762 |
| ALET [mm] | 1.8 | 1.7 | 1.7 | 2.2 | 6.8 | 22.2 | 12.2 | 24.4 | 18.1 | 14.3 | 12.4 | 21.7 | 15.3 |
| $Al_2O_3/SiO_2$ | 0.97 | 1.09 | 1.09 | 0.97 | 0.97 | 0.97 | 0.97 | 0.97 | 0.97 | 0.97 | 0.97 | 1.00 | 0.97 |
| sum component 1 | 38.0 | 34.8 | 34.5 | 30.1 | 35.4 | 27.9 | 32.2 | 26.0 | 30.0 | 31.1 | 32.4 | 26.8 | 31.1 |
| sum component 2 | 39.6 | 39.4 | 39.0 | 31.5 | 44.9 | 35.6 | 48.9 | 39.7 | 41.9 | 39.9 | 37.4 | 35.1 | 39.9 |
| sum component 3 | 9.4 | 9.4 | 9.3 | 28.2 | 8.8 | 26.1 | 7.96 | 24.3 | 17.7 | 18.3 | 19.1 | 27.5 | 18.3 |
| component 4 (F) | 13.0 | 16.4 | 17.2 | 10.3 | 10.9 | 10.3 | 11.0 | 10.1 | 10.3 | 10.6 | 11.1 | 10.6 | 10.6 |

What is claimed is:

1. A glass comprising the following components in % by weight:

| Component | Proportion (% by weight) |
| --- | --- |
| component 1 | 22 to 42 |
| component 2 | 28 to 53 |
| component 3 | 5 to 35 |
| component 4 | 7 to 20 | wherein the proportion (% by weight) component 1 comprises a sum proportion of $SiO_2$ and $P_2O_5$, wherein the proportion (% by weight) component 2 comprises a sum proportion MgO, CaO, SrO, BaO, ZnO, $Al_2O_3$, $Sc_2O_3$, $Y_2O_3$, $La_2O_3$ and $Yb_2O_3$, wherein the proportion (% by weight) of component 3 comprises a sum proportion of $Li_2O$, $Na_2O$, $K_2O$ and $Cs_2O$, wherein the component 4 is F, wherein the glass contains at least one X-ray absorbing component selected from the group consisting of: $Y_2O_3$, $Yb_2O_3$, $La_2O_3$, SrO, BaO, and $Cs_2O$, wherein the total content of $B_2O_3$, ZnO, $ZrO_2$ and $La_2O_3$ is less than 20% by weight, and wherein the glass contains less than 5% by weight of $B_2O_3$.

2. The glass according to claim 1 comprising the following components in % by weight:

| Component | Proportion (% by weight) |
| --- | --- |
| component 1 | 24 to 40 |
| component 2 | 29 to 53 |
| component 3 | 6 to 32 |
| component 4 | 9 to 19. |

3. The glass according to claim 1 comprising the following components in % by weight:

| Component | Proportion (% by weight) |
| --- | --- |
| component 1 | 25 to 37 |
| component 2 | 30 to 51 |
| component 3 | 8 to 30 |
| component 4 | 9.5 to 18. |

4. The glass according to claim 1 comprising the following components in % by weight:

| Component | Proportion (% by weight) |
| --- | --- |
| component 1 | 26 to 35 |
| component 2 | 31 to 48 |
| component 3 | 9 to 29 |
| component 4 | 9.5 to 17.5. |

5. The glass according to claim 1, wherein the component 1 comprises $SiO_2$ and $P_2O_5$ and wherein the component 2 comprises $Al_2O_3$.

6. The glass according to claim 1, comprising the following constituents in % by weight:

| Constituent | Proportion (% by weight) |
| --- | --- |
| $SiO_2$ | 15 to 35 |
| $P_2O_5$ | 3 to 12 |
| $Al_2O_3$ | 15 to 35 |
| CaO | 0 to 13 |
| SrO | 0 to 22 |
| BaO | 0 to 28 |
| $Na_2O$ | 0 to 12 |
| $Cs_2O$ | 0 to 35 |
| F | >5 to 20 | wherein the ratio of the proportion by weight of $Al_2O_3$ to the proportion by weight of $SiO_2$ is higher than 0.75:1.

7. The glass according to claim 1, wherein the ratio of the proportion by weight of $Al_2O_3$ to the proportion by weight of $SiO_2$ is in a range of 0.9:1 to 1.15:1.

8. The glass according to claim 1, wherein the glass contains at least one X-ray absorbing component selected from the group consisting of: $Y_2O_3$, $Yb_2O_3$, $La_2O_3$, SrO, BaO and $Cs_2O$ in a proportion of in total at least 0.1% by weight.

9. The glass according to claim 1, wherein the ratio of the proportion by weight of the component 2 to the proportion by weight of the component 1 is in a range of 1.0:1 to 1.6:1.

10. The glass according to claim 1, wherein the ratio of the proportion by weight of the component 2 to the proportion by weight of the component 3 is in a range of 1.0:1 to 6.5:1.

11. The glass according to claim 1, wherein the ratio of the proportion by weight of the component 1 to the proportion by weight of the component 3 is in a range of 0.8:1 to 4.5:1.

12. The glass according to claim 1, wherein the glass has a refractive index of from 1.43 to 1.55.

13. A glass powder comprising particles of glass powder, wherein the particles of glass powder comprise the glass according to claim 1, and wherein the particle size of the glass powder, when specified as d50 value, is in a range of 0.2 µm to 20 µm.

14. A method of making a glass ionomer cement, comprising the step of:
mixing the glass according to claim 1 with an organic acid.

15. A therapeutic or prosthetic substance mixture comprising the glass according to claim 1.

16. A method of treating cavities in human and/or animal teeth, comprising the step of applying the glass of claim 1 to the teeth.

17. A dental material comprising the glass according to claim 1.

18. A glass ionomer cement comprising the glass according to claim 1.

19. The glass according to claim 1, wherein the proportion of component 4 is in a range of 8 to 20% by weight.

20. The glass according to claim 1, wherein the glass contains $SiO_2$ in a proportion of 28% by weight or less.

* * * * *